United States Patent
Weber et al.

(10) Patent No.: US 11,331,000 B2
(45) Date of Patent: May 17, 2022

(54) TREATMENT COUCH WITH LOCALIZATION ARRAY

(71) Applicant: ACCURAY INCORPORATED, Sunnyvale, CA (US)

(72) Inventors: Adam Jerome Weber, San Jose, CA (US); Eric Earnst, Saratoga, CA (US); Calvin R. Maurer, Jr., San Jose, CA (US); Gopinath Kuduvalli, San Jose, CA (US); Christopher A. Raanes, Portola Valley, CA (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 526 days.

(21) Appl. No.: 15/875,966

(22) Filed: Jan. 19, 2018

(65) Prior Publication Data

US 2018/0140221 A1  May 24, 2018

Related U.S. Application Data

(62) Division of application No. 12/214,771, filed on Jun. 18, 2008, now Pat. No. 9,883,818.
(Continued)

(51) Int. Cl.
*A61B 5/06* (2006.01)
*A61B 6/04* (2006.01)
(Continued)

(52) U.S. Cl.
CPC .............. *A61B 5/06* (2013.01); *A61B 5/062* (2013.01); *A61B 6/04* (2013.01); *A61B 6/547* (2013.01); *A61B 34/20* (2016.02); *A61N 5/1049* (2013.01); *A61B 34/30* (2016.02); *A61B 90/39* (2016.02); *A61B 2034/2051* (2016.02); *A61B 2090/376* (2016.02); *A61B 2090/3762* (2016.02); *A61N 2005/1051* (2013.01)

(58) Field of Classification Search
CPC ............ A61B 34/20; A61B 2034/2051; A61B 2090/376; A61B 2090/3762; A61B 34/30; A61B 5/06; A61B 5/062; A61B 6/04; A61B 6/547; A61B 90/39; A61B 2090/378; A61B 6/0457; A61B 6/08; A61B 6/4405; A61B 6/4464; A61B 6/4476; A61B 6/5247; A61B 6/527; A61B 6/541; A61B 8/0833
See application file for complete search history.

(56) References Cited

U.S. PATENT DOCUMENTS

| | | |
|---|---|---|
| RE30,397 E | 9/1980 | King |
| 4,583,538 A | 4/1986 | Onik et al. |

(Continued)

OTHER PUBLICATIONS

Murphy et al, The accuracy of dose localization for an image-guided frameless radiosurgery system, Medical Physics, 1996, 23 (12):2043-2049.
(Continued)

*Primary Examiner* — Yi-Shan Yang
(74) *Attorney, Agent, or Firm* — Womble Bond Dickinson (US) LLP

(57) ABSTRACT

A method of operating a localization array. The method includes providing the localization array in substantially an optimal position. The method also includes maintaining the localization array at substantially the optimal position by controlling movement of the localization array.

9 Claims, 10 Drawing Sheets

Related U.S. Application Data

(60) Provisional application No. 60/936,388, filed on Jun. 19, 2007.

(51) Int. Cl.
*A61B 6/00* (2006.01)
*A61N 5/10* (2006.01)
*A61B 34/20* (2016.01)
*A61B 90/00* (2016.01)
*A61B 34/30* (2016.01)

(56) References Cited

U.S. PATENT DOCUMENTS

| | | |
|---|---|---|
| 4,770,182 A | 9/1988 | Damadian et al. |
| 4,791,934 A | 12/1988 | Brunnett |
| 4,945,478 A | 7/1990 | Merickel et al. |
| 4,977,505 A | 12/1990 | Pelizzari et al. |
| 5,070,401 A | 12/1991 | Salvati et al. |
| 5,078,140 A | 1/1992 | Kwoh |
| 5,222,499 A | 6/1993 | Allen et al. |
| 5,230,338 A | 7/1993 | Allen et al. |
| 5,261,404 A | 11/1993 | Mick et al. |
| 5,299,253 A | 3/1994 | Wessels |
| 5,313,306 A | 5/1994 | Kuban et al. |
| 5,337,732 A | 8/1994 | Grundfest et al. |
| 5,363,475 A | 11/1994 | Baker et al. |
| 5,389,101 A | 2/1995 | Heilbrun et al. |
| 5,398,684 A | 3/1995 | Hardy |
| 5,417,210 A | 5/1995 | Funda et al. |
| 5,419,320 A | 5/1995 | Kawaguchi et al. |
| 5,454,371 A | 10/1995 | Fenster et al. |
| 5,458,126 A | 10/1995 | Cline et al. |
| 5,491,510 A | 2/1996 | Gove |
| 5,517,016 A | 5/1996 | Lesh et al. |
| 5,531,277 A | 7/1996 | Noonan et al. |
| 5,531,520 A | 7/1996 | Grimson et al. |
| 5,540,229 A | 7/1996 | Collet-Billion et al. |
| 5,546,807 A | 8/1996 | Oxaal et al. |
| 5,562,095 A | 10/1996 | Downey et al. |
| 5,572,999 A | 11/1996 | Funda et al. |
| 5,585,813 A | 12/1996 | Howard |
| 5,604,848 A | 2/1997 | Harada et al. |
| 5,608,849 A | 3/1997 | King, Jr. |
| 5,611,025 A | 3/1997 | Lorensen et al. |
| 5,622,170 A | 4/1997 | Schulz |
| 5,671,381 A | 9/1997 | Strasnick et al. |
| 5,682,886 A | 11/1997 | Delp et al. |
| 5,704,897 A | 1/1998 | Truppe |
| 5,740,802 A | 4/1998 | Nafis et al. |
| 5,772,594 A | 6/1998 | Barrick |
| 5,776,050 A | 7/1998 | Chen et al. |
| 5,781,195 A | 7/1998 | Marvin |
| 5,797,849 A | 8/1998 | Vesely et al. |
| 5,800,352 A | 9/1998 | Ferre et al. |
| 5,815,126 A | 9/1998 | Fan et al. |
| 5,833,608 A | 11/1998 | Acker |
| 5,833,627 A | 11/1998 | Shmulewitz et al. |
| 5,836,954 A | 11/1998 | Heilbrun et al. |
| 5,842,473 A | 12/1998 | Fenster et al. |
| 5,855,553 A | 1/1999 | Tajima et al. |
| 5,868,673 A | 2/1999 | Vesely |
| 5,871,018 A | 2/1999 | Delp et al. |
| 5,882,206 A | 3/1999 | Gillio |
| 5,887,121 A | 3/1999 | Funda et al. |
| 5,891,034 A | 4/1999 | Bucholz |
| 5,892,538 A | 4/1999 | Gibas |
| 6,016,439 A | 1/2000 | Acker |
| 6,106,464 A | 8/2000 | Bass et al. |
| 6,167,296 A | 12/2000 | Shahidi |
| 6,211,666 B1 * | 4/2001 | Acker .................. A61B 5/06 |
| | | 128/899 |
| 6,272,366 B1 | 8/2001 | Vining |
| 6,314,312 B1 | 11/2001 | Wessels et al. |
| 6,359,190 B1 | 3/2002 | Ter-Ovanesyan et al. |
| 6,366,799 B1 * | 4/2002 | Acker .................. A61B 90/36 |
| | | 600/424 |
| 6,516,046 B1 | 2/2003 | Frohlich |
| 6,895,268 B1 | 5/2005 | Rahn et al. |
| 6,932,089 B1 | 8/2005 | Cinquin et al. |
| 7,561,051 B1 * | 7/2009 | Kynor .................. A61B 5/06 |
| | | 340/572.4 |
| 7,623,623 B2 | 11/2009 | Raanes et al. |
| 7,798,970 B2 | 9/2010 | Lo et al. |
| 9,289,268 B2 | 3/2016 | Ramraj et al. |
| 2002/0049375 A1 | 4/2002 | Strommer et al. |
| 2002/0080921 A1 | 6/2002 | Smith |
| 2002/0115931 A1 | 8/2002 | Strauss et al. |
| 2002/0193685 A1 * | 12/2002 | Mate .................. A61N 5/1049 |
| | | 600/424 |
| 2003/0073901 A1 | 4/2003 | Simon et al. |
| 2003/0084906 A1 | 5/2003 | Roe |
| 2003/0130576 A1 | 7/2003 | Seeley et al. |
| 2004/0097806 A1 | 5/2004 | Hunter et al. |
| 2004/0171924 A1 | 9/2004 | Mire et al. |
| 2005/0054895 A1 | 3/2005 | Hoeg et al. |
| 2005/0085717 A1 | 4/2005 | Shahidi |
| 2005/0085718 A1 | 4/2005 | Shahidi |
| 2005/0154293 A1 | 7/2005 | Gisselberg |
| 2005/0182316 A1 | 8/2005 | Burdette et al. |
| 2005/0215888 A1 | 9/2005 | Grimm et al. |
| 2005/0228255 A1 | 10/2005 | Saracen et al. |
| 2006/0004281 A1 | 1/2006 | Saracen |
| 2006/0020210 A1 | 1/2006 | Mendlein et al. |
| 2006/0036162 A1 | 2/2006 | Shahidi |
| 2006/0052694 A1 | 3/2006 | Phillips et al. |
| 2006/0063999 A1 * | 3/2006 | Herron .................. A61N 5/1049 |
| | | 600/407 |
| 2006/0106311 A1 | 5/2006 | Lo et al. |
| 2006/0149418 A1 | 7/2006 | Anvari |
| 2006/0173291 A1 | 8/2006 | Glossop |
| 2006/0285641 A1 | 12/2006 | Scherch |
| 2007/0015991 A1 | 1/2007 | Fun et al. |
| 2007/0038065 A1 | 2/2007 | Creighton et al. |
| 2007/0055144 A1 * | 3/2007 | Neustadter .......... A61N 5/1049 |
| | | 600/425 |
| 2007/0106147 A1 | 5/2007 | Altmann et al. |
| 2007/0211927 A1 | 9/2007 | Groszmann et al. |
| 2007/0276243 A1 | 11/2007 | Gerard et al. |
| 2007/0282192 A1 * | 12/2007 | Rezzonico .......... A61B 5/0555 |
| | | 600/415 |
| 2008/0049896 A1 | 2/2008 | Kuduvalli |
| 2009/0003523 A1 | 1/2009 | Raanes et al. |
| 2009/0069794 A1 | 3/2009 | Kurtz |

OTHER PUBLICATIONS

PCT International Search Report and Written Opinion of the International Searching Authority, PCT/US08/07717 filed Jun. 19, 2008, dated Sep. 23, 2008.

International Preliminary report on Patentability, PCT/US2008/007717, dated Jan. 7, 2010, 7 pages.

"Calypso® 4D Localization System™ ï¿½ Technology Overview", downloaded from http://www.calypsomedical.com/HealthCareTechnology.aspx, 2007, 2 pages.

P. Parikh et al., "Dosimetric effects of a 4D Magnetic Localization System for LINAC Beam Gating on Prostate and Lung Radiation Therapy", Jul. 26, 2007, 1 page.

D.M. Shepard et al., "Latency Measurements and Demonstration of a 4D Electromagnetic Localization System for LINAC Beam Gating", Jul. 25, 2007, 1 page.

E Coste-Maniere et al., Robotic whole body stereotactic radiosurgery: clinical advantages of the CyberKnife® integrated system, Int J Medical Robotics and Computer Assisted Surgery 2005; pp. 28-39.

Jay B West et al., "Designing Optically Tracked Instruments for Image-Guided Surgery", IEEE Transactions on Medical Imaging, vol. 23, No. 5, May 2004, pp. 533-545.

Calypso Abstract, D.M. Shepard et al., "Latency Measurements and Demonstration of a 4D Magnetic Localization System for LINAC beam gating", AAPM 2007 conference, 1 page.

(56) References Cited

OTHER PUBLICATIONS

Calypso Abstract, Latency Measurements and Demonstration of a 4D Magnetic Localization System for LINAC beam gating, AAPM 2007 conference, 2 pages.
Calypso Abstract, Dosimetric effects of a 4D Magnetic Localization System for LINAC beam gating on prostate and lung radiation therapy, AAPM 2007 conference, 2 pages.
Calypso Abstract, Calypso® Medical 4D Localization System, AAPM 2007 conference, 1 page.

* cited by examiner

TREATMENT COUCH WITH LOCALIZATION ARRAY

REFERENCE TO RELATED APPLICATIONS

This application is a divisional of U.S. patent application Ser. No. 12/214,771, which claims the benefit of U.S. Provisional Patent Application No. 60/936,388, which are hereby incorporated by reference.

TECHNICAL FIELD

Embodiments of the present invention relate to the field of radiation treatment, and in particular, to the positioning of an electromagnetic localization array for use in image guided radiation treatment utilizing wireless transponders.

BACKGROUND

Radiotherapy and radiosurgery are non-invasive radiation treatment options widely used to treat patients with a variety of tumors such as brain tumor, lung tumor, and liver tumor. Fiducial tracking is one among a variety of conventional tracking methods utilized in performing radiation treatments.

Electromagnetic tracking systems are used to track the positions of fiducials in near real time (e.g., 10 Hz). In one type of system (i.e., Calypso® 4D Localization System, available from Calypso, of Seattle, Wash.), an array of four transmitter coils spread out in space induces a resonance in a fiducial or transponder coil system. When the magnetic field is switched off, the transponder signal during relaxation is sensed by an array of receiver coils and used to establish the position of the transponder. In the Calypso 4D Localization System, the transmitter and receiver coils are embedded in an array wired to a common device, and the fiducials or transponders are wireless.

A tracking system may provide the positions of fiducials or transponders that are implanted in a patient before acquisition of a treatment planning computed tomography (CT) scan, for example for radiation therapy. The fiducial positions are known relative to the transmitter coils or electromagnetic localization array. If the transmitter coil or array position is known in the treatment room, the fiducial positions relative to the treatment room isocenter (treatment room coordinate system origin) can be obtained. The fiducial positions can then be used to guide treatment, for example, by directing a radiation beam at a target tracked by reference to the fiducial positions.

In such a tracking system, inappropriate placement of the localization array may cause problems such as susceptibility to interference in the array or physical obstruction of other elements of the treatment system.

Another problem with electromagnetic tracking systems is that the accuracy of the position and orientation information is affected by changes in the magnetic field other than those created by the transmitter coils. Perturbations in the magnetic field can be caused by the presence of metal (for example, in radiation therapy, a gantry or robotic manipulator and a linear accelerator) or other conductive material (for example, a treatment table top made out of conductive material). Thus the position information reported by an electromagnetic tracking system in practical use, for example, tracking a target region inside a patient during radiation therapy, can have a higher error than a system specification determined in a carefully controlled laboratory setting.

BRIEF DESCRIPTION OF THE DRAWINGS

The present invention is illustrated by way of example, and not by way of limitation, in the figures of the accompanying drawings.

DETAILED DESCRIPTION

Figure 1:
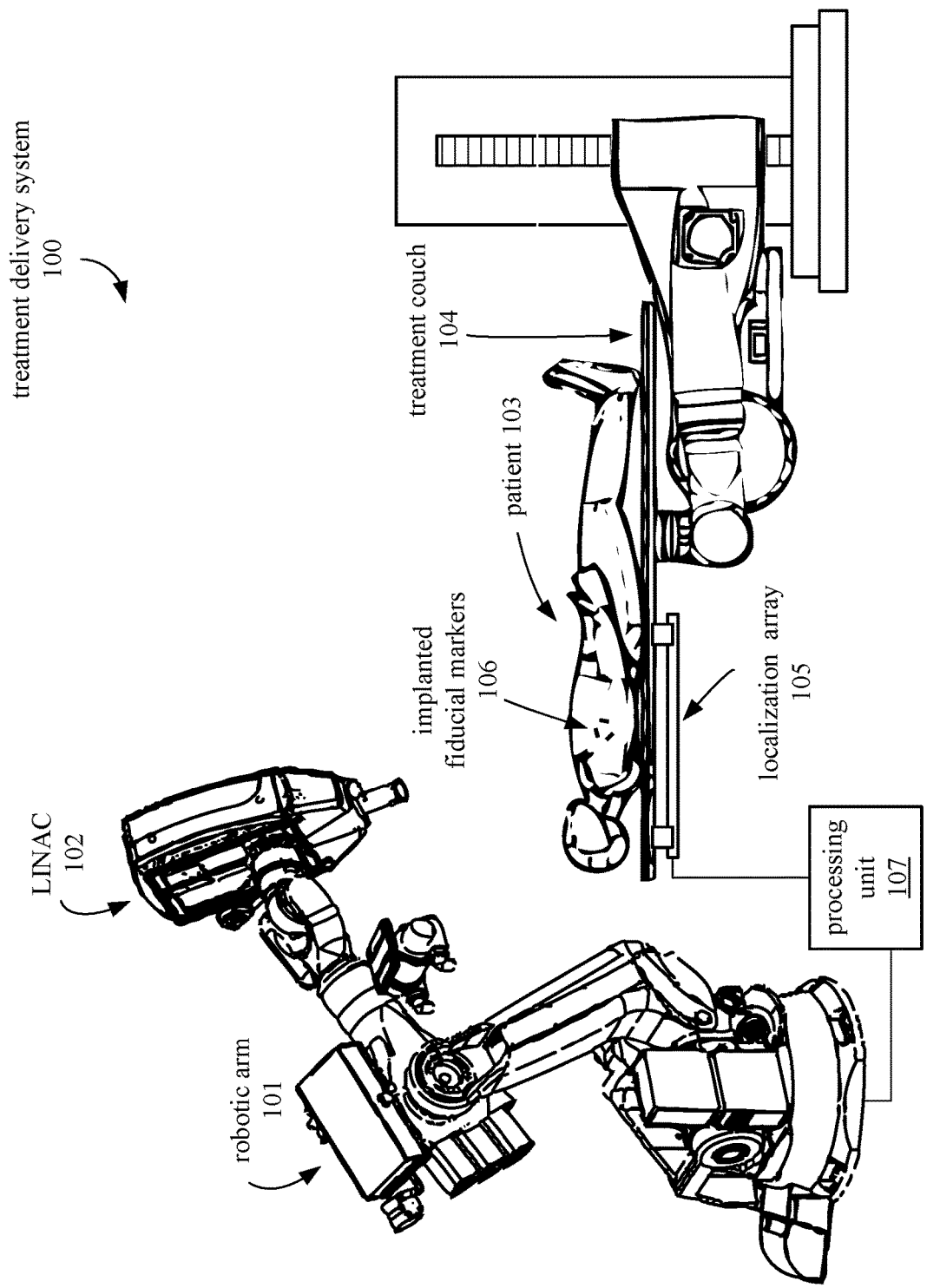
FIG. 1 illustrates a treatment delivery system including localization array for tracking implanted fiducials according to one embodiment of the invention.

Described herein is a method and apparatus for positioning a localization array for use in image guided radiation treatment utilizing wireless transponders. The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

According to one embodiment of the present invention, a localization array to be used for tracking fiducial markers may be coupled with a treatment couch. For example, the localization array may be contained within or attached underneath or above the treatment couch. Such an arrangement may ensure that the localization array maintains its position with respect to the treatment couch, even if the treatment couch moves. Thus, the position of the localization array in the treatment room can be tracked with reference to the treatment couch, rather than tracked independently.

Attachment of the localization array to the treatment couch may also eliminate the need for additional equipment or structures for supporting the array. The presence of such equipment or structures in the treatment room may block imaging equipment, such as an x-ray imager, or may physically obstruct moving equipment, such as a robotic arm for positioning a linear accelerator (LINAC). Accordingly, attachment of the localization array to the treatment couch may also reduce the likelihood of collisions between these pieces of equipment.

Many approaches may be used to couple a localization array to a treatment couch at a desired position. For example, in one embodiment, the localization array may be contained within the treatment couch. In other embodiments, the localization array may be mounted underneath or above the treatment couch. Alternatively, the localization array may also be laid on top of the treatment couch. In this case, a patient undergoing radiation treatment may then lie on top of the localization array. A pad or other covering may be used to separate the patient and the localization array.

The localization array may further be coupled to the treatment couch using an attachment mechanism that allows the localization array to be repositioned while remaining attached to the treatment couch. In other embodiments, the attachment mechanism may also allow the localization array to be detached from the treatment couch entirely and then reattached to the treatment couch at a different location.

FIG. 1 illustrates a radiation treatment delivery system including a localization array for tracking fiducial markers implanted in a patient's body, according to one embodiment of the invention. Treatment delivery system 100 includes robotic arm 101, linear accelerator (LINAC) 102, treatment couch 104 for supporting patient 103, localization array 105 for detection position of implanted fiducial markers 106, and processing unit 107.

Robotic arm 101 carries a LINAC 102 that is capable of producing a beam suitable for use in radiation treatment. Robotic arm 101 is capable of maintaining the direction of the beam of LINAC 102 at a desired target, for example, a tumor within the body of patient 103. Robotic arm 101 may also respond to signals from a target tracking system, such as processing unit 107, to compensate for movement of the target during the treatment process. Treatment couch 104 may be used to support the body of patient 103 during the treatment process and may be a robotic treatment couch. For example, the treatment couch 104 may be a robotic couch capable of movement with at least five degrees of freedom. Alternatively, the treatment couch may be a robotic couch capable of movement with less than five degrees of freedom (e.g., four, three, or fewer degrees of freedom).

In an embodiment where the treatment couch can be repositioned using a robotic arm, the position of the treatment couch in the treatment room can be determined using mechanical encoders such as sensors attached to the robot arm. The sensors may determine the position of the treatment couch and the localization array attached to the couch based on the joint orientations of the robotic arm.

The treatment couch 104 may also respond to signals from a target tracking system to help compensate for movement of the target. Alternatively, treatment couch 104 may be another type of treatment couch, such as the Axum® treatment couch developed by Accuray, Inc. of California. Alternatively, other types of treatment tables may be used.

According to one embodiment of the invention, a localization array 105 may be attached to the treatment couch 104. For example, localization array 105 may be attached to the underside of treatment couch 104 so that the detection field, a volume within which fiducial tracking is most effective, of localization array 105 is directed upwards through the treatment couch 104 and the body of patient 103. The localization array 105 may be placed so that its detection field encompasses implanted fiducial markers 106, which are implanted within the body of patient 103. The localization array can then be used to track the movement of implanted fiducial markers 106, and may include transmitter coils, receiver coils, or both transmitter and receiver coils for this purpose. Alternatively, transmitter coils may be removed from localization array 105, so long as the signal from the transmitter coils can still reach the implanted fiducial markers 106. Processing unit 107 may be used to collect tracking data from localization array 105 and direct robotic arm 101 to reposition the beam of LINAC 102 according to the most recently determined target position. The position of the target may, for example, be determined in reference to the implanted fiducials 106 if the target has a known location with respect to the implanted fiducials 106.

Figure 2:
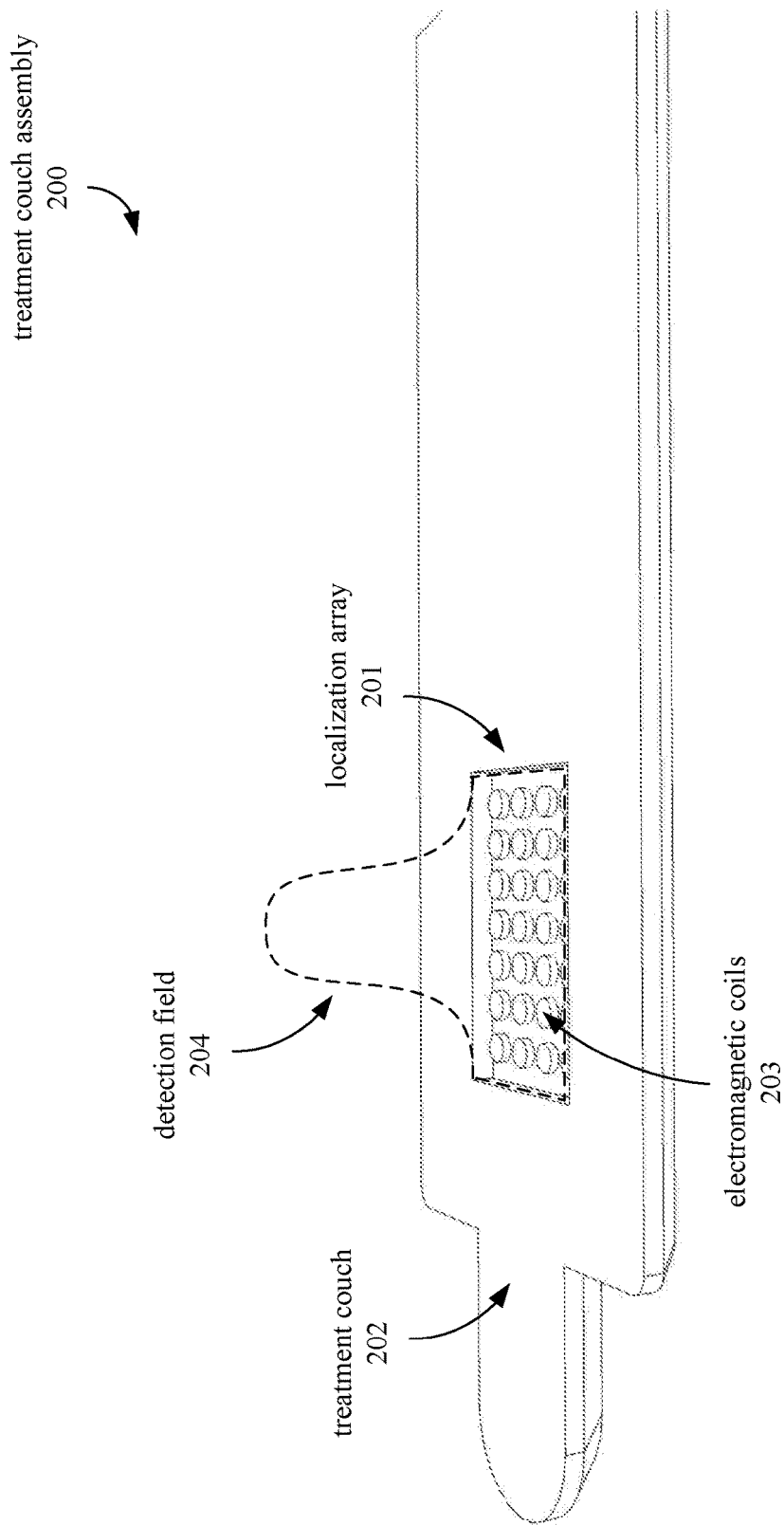
FIG. 2 illustrates a localization array integrated within a treatment couch according to one embodiment of the invention.

FIG. 2 illustrates a treatment couch assembly including an integrated localization array according to one embodiment of the invention. Treatment couch assembly 200 includes localization array 201, which is contained within treatment couch 202. Localization array 201 contains electromagnetic coils 203 which may be used for tracking of fiducial markers located within detection field 204. Electromagnetic coils 203 may include transmitter coils, receiver coils, or a combination of transmitter and receiver coils.

In FIG. 2, localization array 201 is exposed for clarity, although in some embodiments, localization array 201 may be concealed beneath the surface of treatment couch 202. Alternatively, localization array 201 may also be laid on top of treatment couch 202 and may or may not be secured to treatment couch 202. Whether laid on top or integrated within treatment couch 202, localization array 201 may be covered. For example, localization array 201 may be covered to protect from physical damage or for aesthetic reasons. The covering material may be chosen to have minimal effect on the fiducial tracking capability of the localization array 201. The covering material may also be chosen for the comfort of a patient 103 or to protect the patient 103 or the localization array 201. For example, the covering may be a pad placed over the localization array 201. Localization array 201 may also be centered with respect to treatment couch 202 along one or more axes of treatment couch 202. For example, localization array 201 may be centered along the width of treatment couch 202.

Localization array 201 may, in one embodiment, cover or underlie only a portion of the surface of treatment couch 202. Alternatively, localization array 201 may cover or underlie the entire surface of treatment couch 202. While in one embodiment, treatment couch 202 contains only one localization array 201, other embodiments of treatment couch 202 may contain more than one localization array 201.

During a treatment session, a patient 103 may lie on treatment couch 202 so that implanted fiducial markers 106 implanted in the body of patient 103 are within the detection field 204 of localization array 201. Localization array 201 may then be used to track the locations of implanted fiducials 106.

Figure 3A:
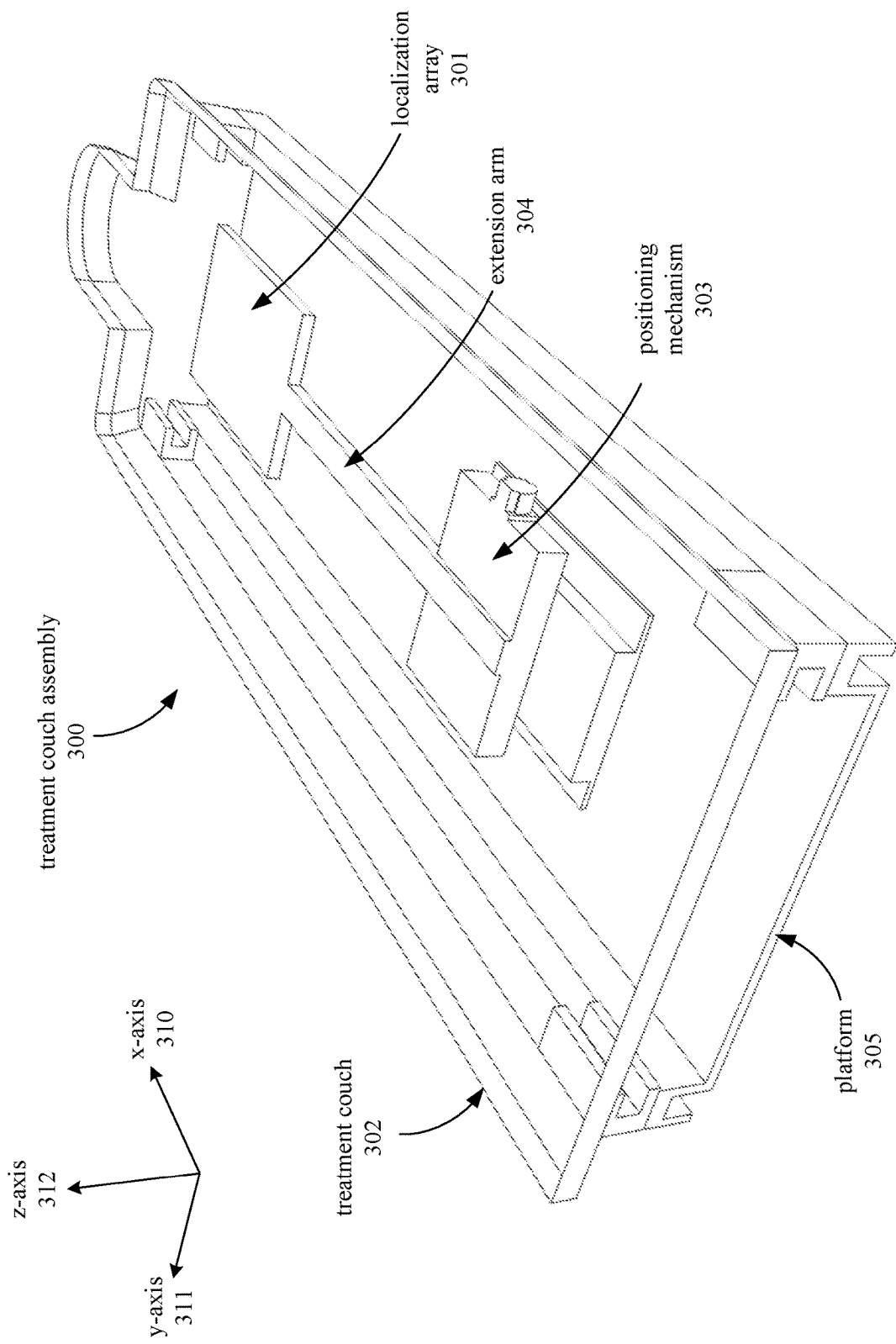
FIG. 3A illustrates a localization array mounted underneath a treatment couch using a motorized attachment mechanism according to one embodiment of the invention.

FIG. 3A illustrates a treatment couch assembly that includes a localization array mounted underneath the surface of a treatment couch according to one embodiment of the invention. Treatment couch assembly 300 includes a localization array 301 mounted underneath a treatment couch 302. Localization array 301 may be attached to a positioning mechanism 303 through an extension arm 304. Positioning mechanism 303 may be mounted on a platform 305 attached to treatment couch 302.

Localization array 301 may be positioned underneath the surface of treatment couch 302 so that the detection field of localization array 301 extends through and above the surface of treatment couch 302. Localization array 301 may include transmitter coils, receiver coils, or both transmitter and receiver coils. Localization array 301 may also be attached to a positioning mechanism 303. In one embodiment, positioning mechanism 303 may be mounted on platform 305. Alternatively, positioning mechanism 303 may be mounted on the underside of treatment couch 302. Platform 305 may be rigidly attached to treatment couch 302 so that positioning mechanism 303 does not move with respect to treatment couch 302. Thus, repositioning of localization array 301 may occur solely through the operation of positioning mechanism 303. In alternative embodiments, positioning mechanism 303 may be attached to treatment couch 302 in a manner that allows movement between treatment couch 302 and positioning mechanism 303 and localization array 301. For example, treatment couch 302 may be mounted on slides that allow treatment couch 302 to move along the x-axis 310 with respect to positioning mechanism 303 and localization array 301. Positioning mechanism 303 may operate to move localization array 301 with respect to the treatment couch 302. For example, positioning mechanism 303 may move localization array 301 along the x-axis 310 or y-axis 311. Thus, during a radiation treatment session, the localization array 301 may be moved to a desired position so that its detection field may encompass fiducial markers being tracked without moving the patient or the treatment couch 302. Positioning mechanism 303 may also operate to move localization array 301 outside the imaging field of other imaging devices in the treatment room. For example, if an x-ray imager is in use, the localization array 301 may be moved out of the imaging field of the x-ray imager so that the localization array 301 is not captured in the x-ray image. Localization array 301 may also be moved for other reasons, such as to avoid obstructing moving equipment or personnel. Positioning mechanism 303 may also operate to move localization array 301 in the direction indicated by z-axis 312 in order to bring localization array 301 closer to or farther away from treatment couch 302.

Positioning mechanism 303 may in one embodiment be implemented using an X-Y table. Alternatively, other mechanisms such as robots or non-motorized manual positioning mechanisms may be used. Positioning mechanism 303 may also accept inputs from a computer or other device in order to automate the movement of localization array 301 during a treatment session. Furthermore, positioning mechanism 303 may also send signals to another device to indicate the position of localization array 301. In one embodiment, mechanical encoders are used to determine the position of the localization array in the treatment room. For example, positioning mechanism 303 may utilize servo motors capable of indicating the rotational positions of the motors, which can then be used to calculate the position of the localization array 301. Alternatively, other methods for determining the location of localization array 310 may be used in conjunction with positioning mechanism 303, such as positioning marks or optical sensors.

Localization array 301 may be attached to positioning mechanism 303 using an extension arm 304. Extension arm 304 may be used so that localization array 301 is kept away from positioning mechanism 303. For example, in cases where the operation or structure of positioning mechanism 303 may degrade the electromagnetic signals received by localization array 301, extension arm 304 may enable localization array 301 to be sufficiently removed from positioning mechanism 303 so that the electromagnetic signals are unaffected by positioning mechanism 303. Alternatively, localization array 301 may in other embodiments be attached to positioning mechanism 303 without using extension arm 304.

Figure 3B:
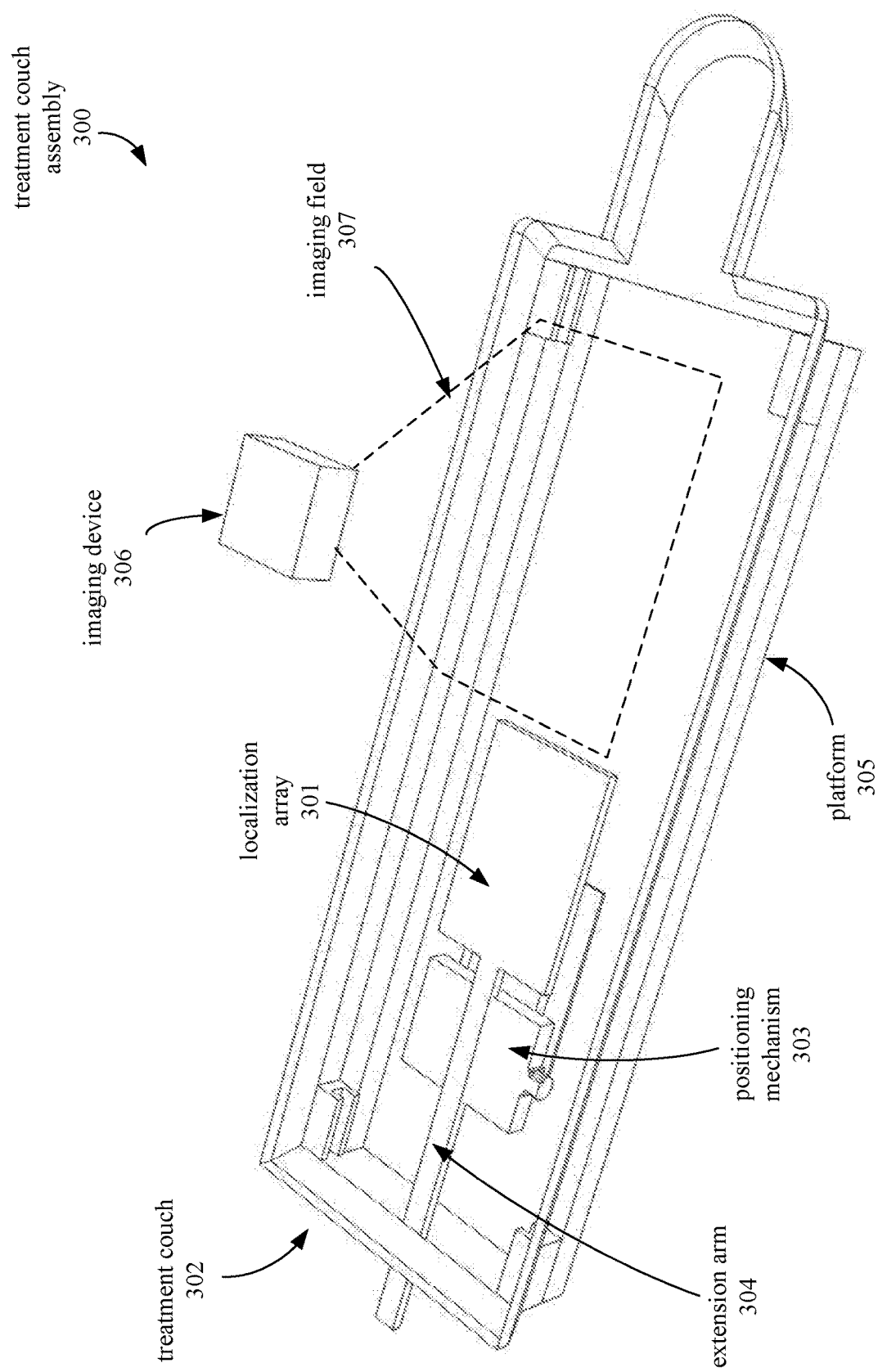
FIG. 3B illustrates a localization array mounted underneath a treatment couch using a motorized attachment mechanism according to one embodiment of the invention where the localization array is positioned beyond an imaging field of an imaging device.

FIG. 3B illustrates a treatment couch assembly where the localization array is positioned beyond an imaging field of an imaging device according to one embodiment of the invention. Imaging device 306 is configured to capture images from within imaging field 307. Imaging device 306 may be a device such as an x-ray imager.

Localization array 301 may be moved using positioning mechanism 303 so that localization array 301 is positioned beyond imaging field 307. With the localization array 301 in this position, imaging device 306 may avoid capturing localization array 301 in an image. For example, imaging device 306 may be used to capture images of a patient's anatomy while the patient is lying on treatment couch 302. In this case, allowing localization array 301 to remain in the imaging field may obscure the anatomical features which are the desired subject of the resulting image.

Figure 3C:
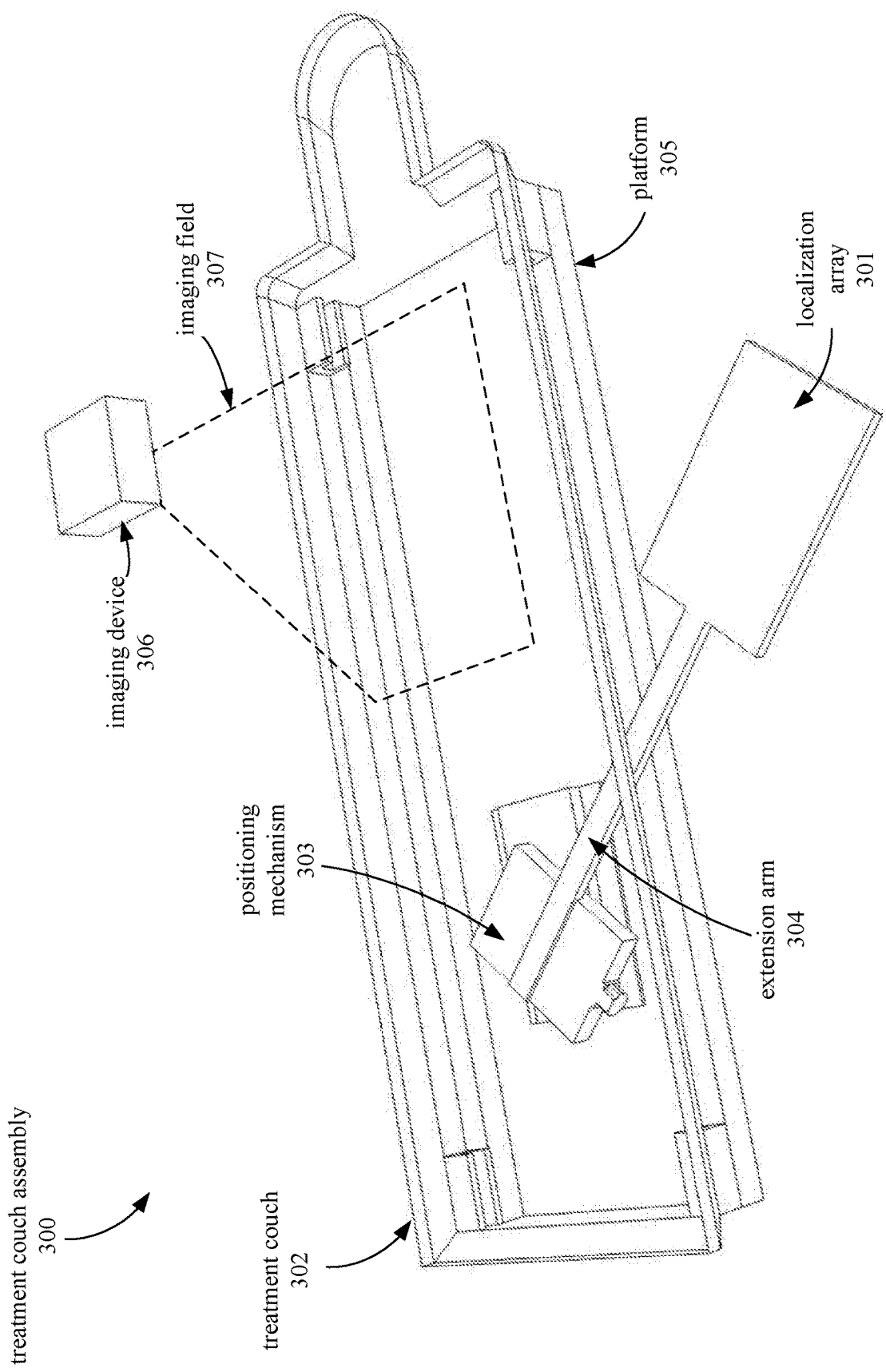
FIG. 3C illustrates a localization array mounted underneath a treatment couch using a motorized attachment mechanism according to one embodiment of the invention where the localization array is rotated beyond an imaging field of an imaging device.

FIG. 3C illustrates a treatment couch assembly having a localization array that is rotated beyond an imaging field of an imaging device according to one embodiment of the invention. A rotational movement may also be used to position localization array 301 outside the imaging field 307 of imaging device 306. For example, positioning mechanism 303 may include a swivel connection to allow positioning mechanism 303 to swing localization array 301 out of the imaging field 307.

Figure 4:
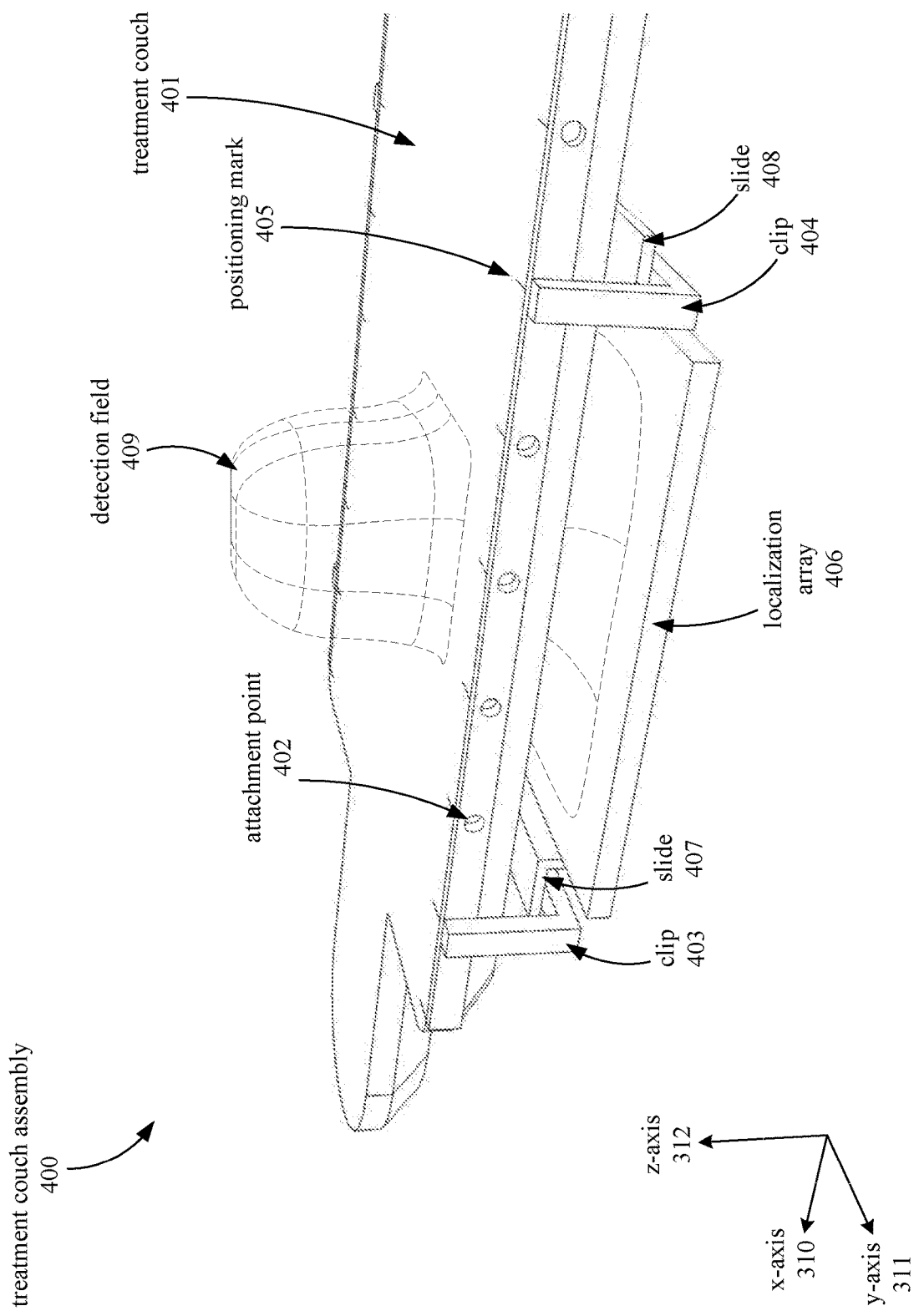
FIG. 4 illustrates a localization array attached to a treatment couch by an attachment mechanism according to one embodiment of the invention.

FIG. 4 illustrates a treatment couch assembly including a localization array that is secured to the treatment couch using an attachment mechanism. Treatment couch assembly 400 includes treatment couch 401 having a number of attachment points such as attachment point 402, clips 403 and 404, a number of positioning marks such as positioning mark 405, localization array 406, and slides 407 and 408. Clips 403 and 404 and slides 407 and 408 constitute an attachment mechanism for securing localization array 406 to treatment couch 401. Localization array 406 has a detection field 409.

Treatment couch 401 may have a number of attachment points such as attachment point 402, where clips 403 and 404 may be attached. Localization array 406 may then be attached to clips 403 and 404. The attachment points may be located at evenly spaced positions on both sides of treatment couch 401. Each attachment point may also have a corresponding positioning mark such as positioning mark 405. The positioning marks may also be labeled with numbers or other symbols used to identify the attachment points. Identifying attachment points where clips 403 and 404 are attached may further facilitate determining the location of the localization array 406 with respect to treatment couch 401. This relative location may ultimately be used to locate fiducial markers such as implanted fiducials 106 tracked by the localization array 406 with respect to the beam of LINAC 102 during a radiation treatment session. In one embodiment, the position of the localization array 406 with respect to the treatment couch may be determined using mechanical encoders. For example, the attachment points or clips 403 and 404 may have sensors to indicate to which attachment points the localization array 406 is attached. Alternatively, if the position of the localization array 406 relative to the treatment couch is known, the position of the couch in the treatment room can be determined using mechanical encoders. For example, if the couch is movable on a track, sensors on the track can be used to identify the position of the couch on the sliders. The position of the localization array in the treatment room then can be determined by reference to the position of the treatment couch.

The clips 403 and 404 may be attached to the attachment points using fasteners. For example, hooks or screw-type fasteners may be used to attach clips 403 and 404 to the attachment points. Other types of fasteners may also be used. The fasteners may be selected based on their ability to support the weight of localization array 406 and clips 403 and 404. In one embodiment, clips 403 and 404 may be separate from localization array 406 such that clips 403 and 404 may be attached to treatment couch 401 independently from localization array 406. In other embodiments, clips 403 and 404 and localization array 406 may be a single assembly to be attached to treatment couch 401 in a single piece.

Localization array 406 may be repositioned along the x-axis 310 with respect to the treatment couch 401 by detaching clips 403 and 404, and then reattaching clips 403 and 404 at different attachment points. Localization array 406 may also be repositioned along the z-axis 312 by exchanging clips 403 and 404 with a set of shorter or longer clips. Alternatively, clips 403 and 404 may be adjustable in length so that the same clips 403 and 404 may be used to adjust the position of localization array 406 along the z-axis 312. Localization array 406 may be equipped with slides 407 and 408 to support localization array 406 on clips 403 and 404 while allowing localization array 406 to be repositioned along the y-axis 311 relative to the treatment couch 401. Using these and other mechanisms known in the art, localization array 406 may be repositioned so that its detection field 409 is in an optimal position for tracking a set of fiducial markers.

Figure 5:
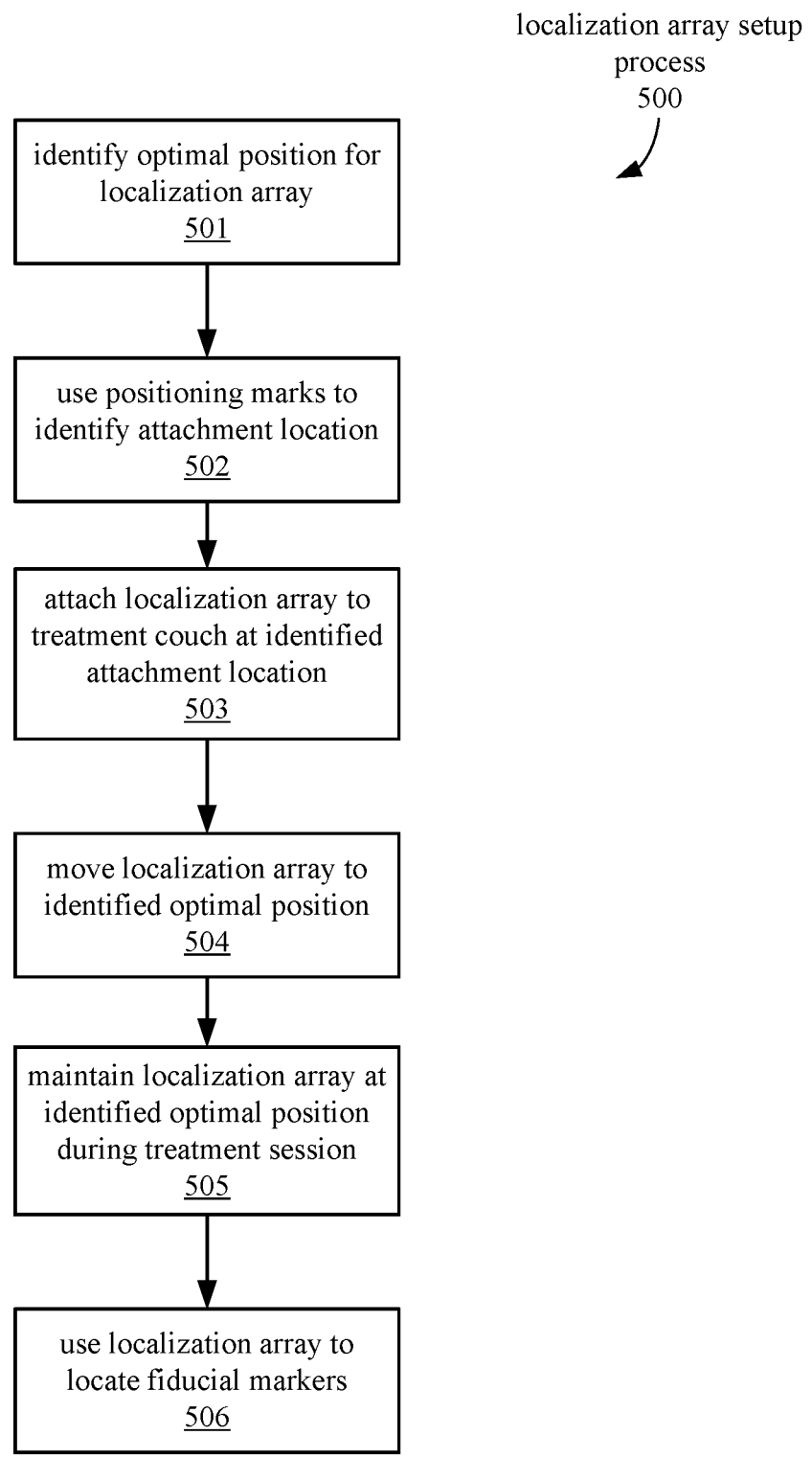
FIG. 5 is a flow chart illustrating a process for using a localization array and treatment couch assembly according to one embodiment of the invention.

FIG. 5 is a flow chart illustrating a process for setting up and using an electromagnetic localization array and treatment couch assembly according to one embodiment of the invention. Localization array setup process 500 begins with block 501, where an optimal position for a localization array such as localization array 105 is determined. In one embodiment, the optimal position for localization array 105 may be a position where the detection field of localization array 105 encompasses implanted fiducial markers 106. Alternatively, an optimal position for a localization array may be determined based on other factors or a combination of factors. For example, the optimal position may be determined based on a desired characteristic of a signal received by the localization array 105 from the implanted fiducials 106. The optimal position may also be chosen to avoid obstruction by the localization array 105 of imaging equipment or moving equipment such as robotic arm 101.

After the optimal position for the localization array is identified in block 501, execution proceeds to block 502, where positioning marks may be used to identify an attachment location for the localization array. For example, in one embodiment, positioning marks such as positioning mark 405 may identify one or more attachment points such as attachment point 402 where clips 403 and 404 may be attached so that localization array 406 is positioned at the optimal position. In other embodiments, positioning marks may not be required to identify an attachment location because the localization array may already be attached to the treatment couch. For example, the localization array may be integrated into the treatment couch, such as localization array 201, or the localization array may be designed to remain attached to the treatment couch between treatment sessions. In these cases, localization array setup process 500 may not require block 502.

Following block 502 is block 503, where the localization array may be attached to the attachment location identified in block 502. For example, clips 403 and 404 supporting localization array 406 may be attached to attachment points identified in block 502 so that the localization array 406 can be positioned at the optimal position identified in block 501. In some embodiments, localization array setup process 500 may not require block 503 because the localization array may already be attached to the treatment couch.

From block 503, execution may proceed to block 504, where the localization array may be moved to the identified optimal position. At this stage, the localization array may already be attached to the treatment couch. Thus, moving the localization array to the optimal position identified in block 501 may entail using a positioning mechanism, such as positioning mechanism 303 or slides 407 and 408, to move the localization array along one or more axes in relation to the treatment couch.

After the localization array has been moved to the optimal position, execution may proceed to block 505, where the localization array is maintained at the optimal position during a treatment session. The position of the localization array may be maintained in accord with block 505 for only a portion of the entire treatment session. For example, if the fiducial markers move during the treatment session, the position of the localization array may be adjusted to compensate for the movement before the end of the treatment session. Furthermore, the localization array needs only to be sufficiently stationary to allow tracking of fiducial markers. For example, processing unit 107 or another part of the tracking system may tolerate or compensate for small movements of the localization array 105. The position of the localization array may be maintained by physically immobilizing the localization array with respect to the treatment couch. For example, if the localization array is attached to the treatment couch through a positioning mechanism such as positioning mechanism 303, the positioning mechanism may be turned off or locked in place. If the localization array is equipped with slides such as slides 407 and 408, then the slides may be locked, clamped, or otherwise immobilized to prevent movement of the localization array. Alternatively, the localization array may maintain its position without further action. For example, locking or clamping of slides 407 and 408 may not be required if friction is sufficient to prevent undesired movement of localization array 406. Also, if the localization array is integrated into the treatment couch, such as localization array 201, the localization array may already be immobilized with respect to the treatment couch.

While the localization array is being maintained in a known position, the localization array may be used to track locations of fiducial markers relative to the localization array, as provided in block 506. If the position of the localization array relative to the treatment couch and the position of the treatment couch relative to other equipment are also known, then the locations of the tracked fiducial markers relative to other equipment may be determined. For example, the locations of the fiducial markers may be determined relative to the location of a LINAC administering radiation treatment. Block 506 may also be repeated during the course of the treatment session so that the location of the fiducial markers can be periodically updated. Thus, maintaining the localization array in a stable position relative to the treatment couch may eliminate the need for recalculating or re-detecting the positional offset of the localization array from the treatment couch each time the locations of the fiducial markers are determined. Furthermore, if the localization array is attached to the treatment couch, the localization array may maintain its positional offset relative to the treatment couch even if the treatment couch is moved during the treatment session. Another advantage of maintaining the positional offset between the localization array and the treatment table is that the fiducial markers within the detection field of the localization array may remain within the detection field of the localization array even if the treatment couch is moved. For example, implanted fiducial markers 106 within patient 103 lying on treatment couch 104 may be encompassed by the detection field of localization array 105. If localization array 105 is attached to treatment couch 104, then patient 103, implanted fiducials 106, localization array 105, and the detection field of localization array 105 may all move concurrently with treatment couch 104. Thus, the detection field will continue to encompass the implanted markers 106 even if the treatment couch 104 is moved, facilitating reliable tracking of the implanted fiducials 106. By tracking the locations of fiducial markers, a treatment delivery system such as treatment delivery system 100 may then use robotic arm 101 to position LINAC 102 to deliver radiation to a target that can be located with reference to the implanted fiducials 106.

Figure 6:
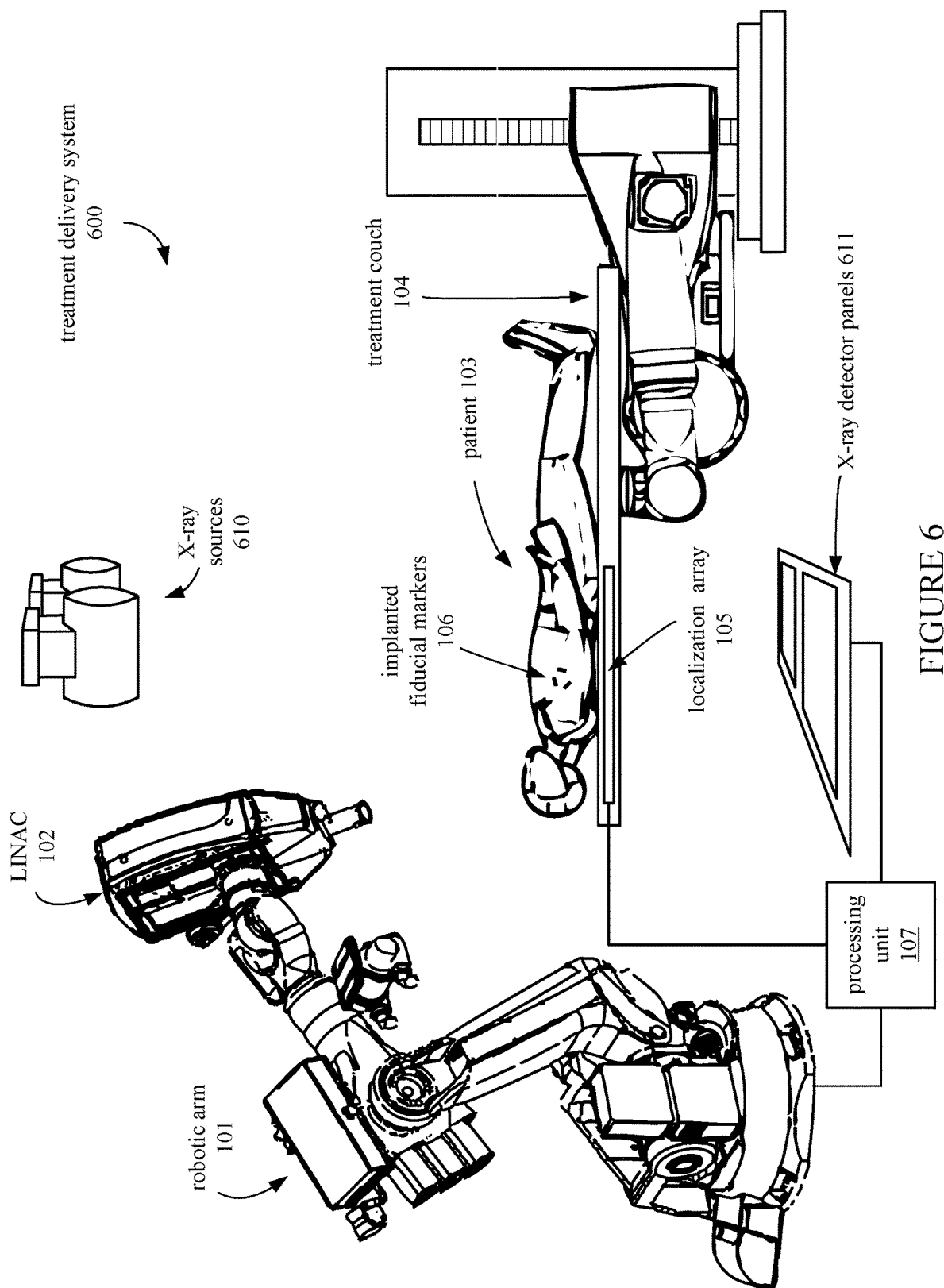
FIG. 6 illustrates one embodiment of a treatment delivery system with an electromagnetic tracking system capable of compensating for positional information error.

FIG. 6 illustrates one embodiment of a treatment delivery system with a localization array. Treatment delivery system 600 is configured to compensate for positional information error in an electromagnetic tracking system resulting from perturbations in the electromagnetic tracking system's magnetic field. Such distortions of the magnetic field tend to increase error in the determination of the position of implanted fiducials by the electromagnetic tracking system. The electromagnetic tracking system of treatment delivery system 600 may include a processing unit 107, localization array 105.

In one embodiment, the bias or offset error caused by perturbations in the magnetic field may be initially compensated by calibrating or characterizing the effect of the treatment delivery system (e.g., gantry system or robot-mounted LINAC 102), which could for example be a one-time procedure involving precalibration and storage of distortion offset for one or more possible positions of a gantry or robotic arm. In some embodiments, electromagnetic disturbances caused by equipment can be minimized by constructing the equipment from low conductivity or non-conductive materials. For example, the treatment couch 104 may be constructed from Kevlar. As compared to other light-weight materials, such as carbon-fiber, Kevlar is less conductive and thus tends to cause less distortion in the electromagnetic field. Nevertheless, additional sources of magnetic field distortion may not be accounted for through material selection for the treatment couch. A possible additional source of error is metal implants inside a patient (e.g., hip prosthesis), for which changing the material of the treatment couch or precalibrating the system may not be feasible.

In another embodiment, an independent fiducial localization method is used in order to compute the distortion offset. The positions of the implanted fiducial may obtained through use of an imaging system (e.g., X-ray, x-ray computed tomography, etc.) that can localize the implanted fiducials with very high accuracy (e.g., several tenths of a millimeter or better). The difference between the imaging acquired implanted fiducial positions and the fiducial positions determined using localization array 105 is, thus, the bias or offset of the electromagnetic tracking positions. An x-ray imager is discussed hereafter for ease of explanation purposes. It should be noted again that other imaging modalities and systems such as cone-beam CT (i.e., x-ray imaging system rotated about the patient to generate a cone-beam CT) and ultrasound may be used.

One embodiment of an X-ray imaging system includes both an X-ray source and an X-ray detector panel. Treatment delivery system 600 includes X-ray sources 610 and X-ray detector panels 611. The X-ray sources 610 may be mounted angularly apart, for example, about 90 degrees apart, and aimed through the treatment target (e.g., tumor within the patient) toward the X-ray detector panels 611. Alternatively, a single large detector may be used that would be illuminated by each of the X-ray sources 610. In the single detector imaging system, the X-ray sources 610 may be positioned apart at an angle less than 90 degrees to keep both images on the single detector surface.

The detector panels 611 may be placed below the treatment target (e.g., on the floor), on the treatment couch 104, or underneath the LINAC 102, and the X-ray sources 610 may be positioned above the treatment target (e.g., the ceiling of the treatment room), to minimize magnification of the images and, therefore, the required size of the detector panels 611. In an alternative embodiment, the positions of the X-ray sources 610 and the detector panels 611 may be reversed, e.g. the X-ray sources 610 below the treatment target and the detector panels 611 above the treatment target. In another embodiment, the detector panels 611 are arranged in a manner such that they move into position for imaging and are moved out of the way during positioning of the LINAC 102 or the treatment couch 104 or during delivery of the radiation beam from the LINAC 102.

By using two X-ray imagers, which could be mounted approximately orthogonally, the 2D positions of the implanted fiducials 106 in the X-ray images can be back projected to obtain their 3D positions in the treatment room. The fiducial positions obtained using x-ray image localization can be known with very high accuracy (several tenths of a millimeter or better). The difference between the X-ray image-based fiducial positions and the fiducial positions determined using localization array 105 is thus the bias or offset of the electromagnetic tracking positions. In one embodiment, the electromagnetic bias or offset is calculated by processing unit 107, which may be connected to localization array 105 and X-ray detector panels 611. Thus, processing unit 107 may receive the locations of the implanted fiducials 106 as determined by the localization array 105 and as determined by X-ray imaging. Processing unit 107 may further use the calculated electromagnetic bias or offset in controlling robotic arm 101 to direct the beam of LINAC 102 at a treatment target.

The electromagnetic bias often changes slowly with spatial location. Thus, for small motions, the offset can be used to correct the real-time electromagnetic tracking positions, as determined using the localization array 105. Since electromagnetic tracking with the localization array 105 does not involve radiation exposure to the patient, it may be used to track the positions of implanted fiducials 106 in near real time. The use of electromagnetic tracking to avoid the use of X-ray imaging is desirable because very frequent X-ray images of the patient may result in excessive radiation exposure to the patient. Any bias in the electromagnetic tracking positions can be corrected by taking occasional X-ray images to locate the implanted fiducials 106 with greater accuracy. The frequency of the X-ray images can be varied as necessary, for example, at every position of the treatment delivery system (e.g., gantry or LINAC 102). Alternatively, X-ray images may be captured periodically over time. New X-ray images could also be acquired whenever the electromagnetic tracking fiducials move beyond a certain threshold. Note that using an X-ray imaging system also requires that the treatment couch (e.g., in the form of a table or chair) be relatively radiolucent.

In order to determine the fiducial positions relative to the treatment room coordinate system, the position of localization array 105 in the treatment room needs to be known. The location of the localization array 105 can be obtained, for example, by tracking the array with an optical tracking system. However, this requires a line of sight between the array and the optical system. Placing the localization array 105 under the patient 103 is desirable for many reasons. This placement reduces potential collision issues with the treatment delivery system (gantry system or robotic arm 101 with LINAC 102). Placing the localization array 105 under the patient 103 could be accomplished by placing the array 105 on the treatment couch 104 and placing a pad over the array 105. The localization array 105 could also be integrated into the treatment couch 104. The localization array 105 may be movable to accommodate different patient sizes and setup positions and different treatment target positions. For example, localization array 105 could be placed in a platform or housing such that it can be easily moved along the long axis of the table and possibly also along the short axis of the table. Placing the array 105 under the patient 103, whether on or integrated into the treatment couch 104, may require a non-optical method for obtaining the position of the array 105 in the treatment room. One non-optical method for tracking the position of array 105 is to use one or more (e.g., two) X-ray imagers.

Figure 7:
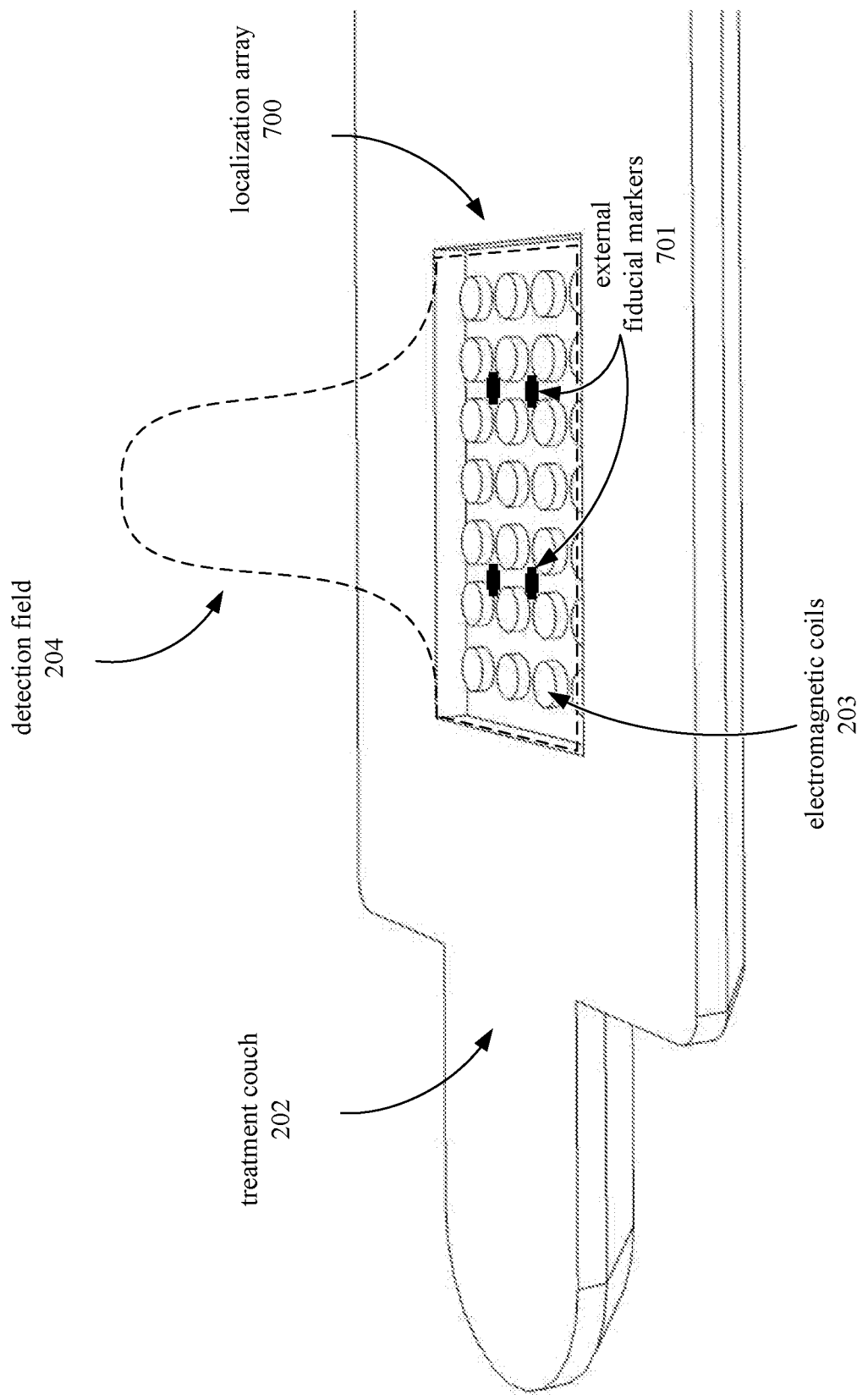
FIG. 7 illustrates one embodiment of a localization array with embedded fiducial markers.

FIG. 7 illustrates one embodiment of a localization array 700 that can be tracked using X-ray imaging. Localization array 700 includes fiducial markers 701 that are located outside of patient 103, and also includes electromagnetic coils 203. Localization array 700 is integrated in treatment couch 202 so that detection field 204 encompasses an area above treatment couch 202.

With external fiducial markers 701 embedded in array 700, the position of array 700 can be tracked using a tracking device such as an X-ray imager. It should be noted that the term "external fiducial markers" is used herein to distinguish from the implanted fiducials that are internal to a patient. Accordingly, an external fiducial marker is one which is disposed outside of a patient's body. External fiducial markers 701 may be made from a radio-opaque material so that external fiducials 701 will appear in X-ray images. By using two X-ray imagers, which could be mounted approximately orthogonally, the 2D positions of the external fiducials 701 in the X-ray images can be back projected to obtain their 3D positions. The 3D positions are transformed to the treatment room coordinate system and, thus, the position of the localization array 700 in the treatment room coordinate system is determined. Such transformations are known in the art; accordingly, a detailed description is not provided herein. Alternatively, electromagnetic coils 203 in the array 700 could be used as fiducials to be tracked by a tracking device. If the tracking device is an X-ray imager, the coils may be uniquely distinguishable radiographically. For example, each of the electromagnetic coils 203 may have a unique shape so that the coil and its position can be uniquely identified in an X-ray image. The position of localization array 700 could be determined with other methods as well. In one embodiment, if the localization array 700 is integrated into the treatment couch 202 and is movable with respect to treatment couch 202, a position tracking device may include mechanical encoders which can be used to obtain the position of the localization array 700 relative to the treatment couch 202. Mechanical encoders may also be used to determine the position of treatment couch 202 in the treatment room. Treatment couch 202 could be a conventional treatment table, or could be a table top mounted on a robotic manipulator.

Thus, the position of localization array 700 relative to the treatment room coordinate system and the positions of implanted fiducial markers 106 in patient 103 relative to localization array 700, as electromagnetically tracked by the localization array, can be used to determine the positions of implanted fiducials 106 relative to the treatment room coordinate system. In addition, bias or offset error in the electromagnetically tracked position of the implanted fiducials 106 caused by disturbances in the electromagnetic field can be corrected by using occasional X-ray images to more accurately locate the implanted fiducials 106. This method for determining the location of the implanted fiducials 106 may be used not only with localization arrays that are integrated with treatment couch 104, but also with localization arrays that are not coupled to the treatment couch 104.

Figure 8:
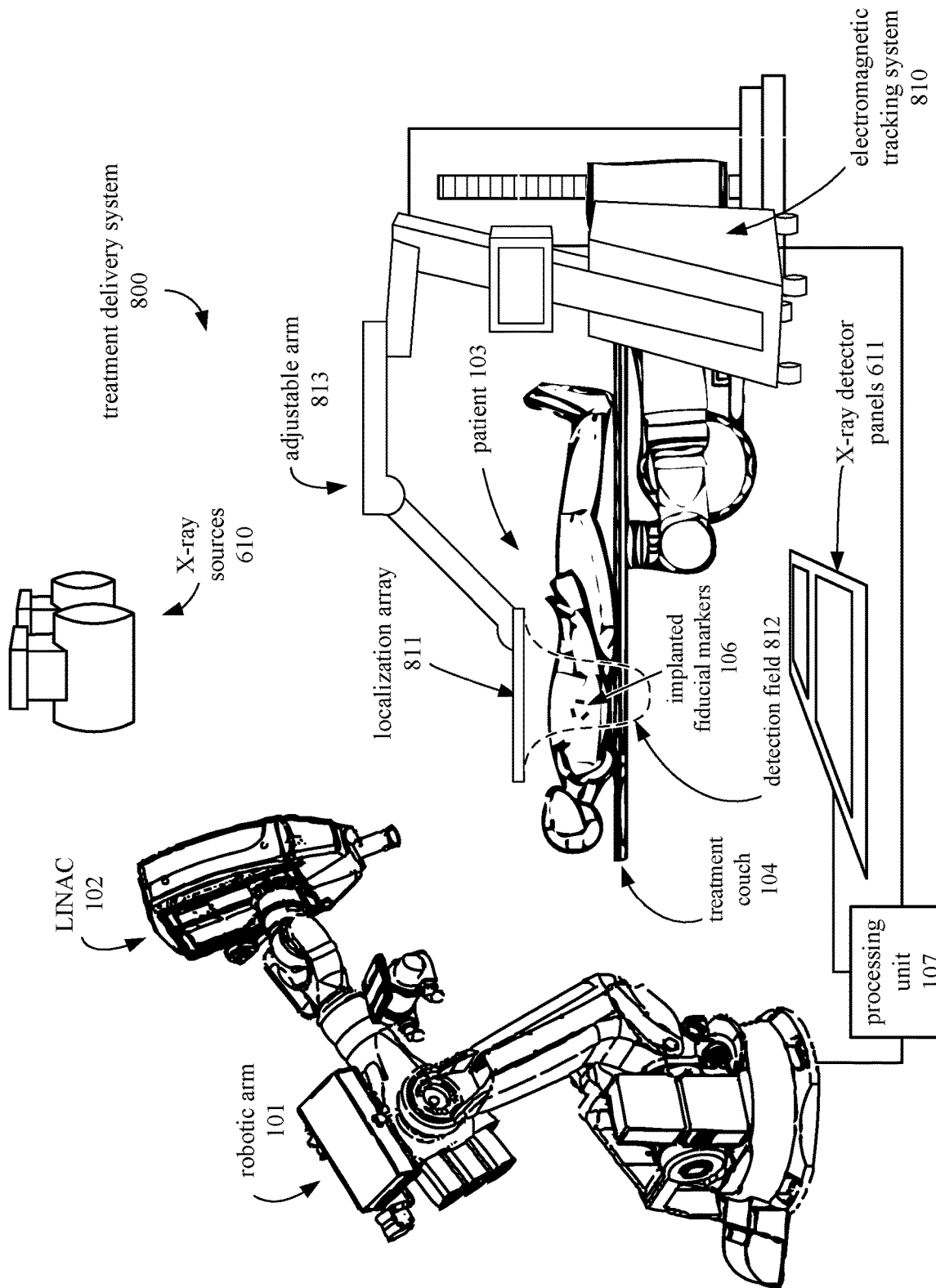
FIG. 8 illustrates one embodiment of a treatment delivery system with an electromagnetic tracking system capable of compensating for positional information error.

FIG. 8 illustrates a treatment delivery system capable of tracking the location of fiducial markers using a localization array external to the treatment couch, in conjunction with X-ray imaging according to one embodiment of the invention. Treatment delivery system 800 includes electromagnetic tracking system 810 connected to localization array 811. Localization array 811 has a detection field 812 that extends downwards to encompass implanted fiducials 106. Treatment delivery system 800 also includes X-ray imagers comprising X-ray sources 610 and X-ray detector panels 611.

Localization array 811 may be similar to localization array 700, having electromagnetic coils that can be used to determine the positions of implanted fiducials 106. Localization array 811 is not attached to treatment couch 104, and thus may be moved independently of treatment couch 104. In one embodiment, localization array 811 is mechanically supported by electromagnetic tracking system 810. For example, localization array 811 may be mounted on an adjustable arm 813 connected to electromagnetic tracking system 810, which allows localization array 811 to be situated above patient 103. Accordingly, localization array 811 may have a detection field 812 that extends downward to encompass implanted fiducials 106 so that localization array 811 can track the positions of implanted fiducials 106. Electromagnetic tracking system 810 that is attached to localization array 811 may be an external unit containing electronics, such as drive circuitry and sensors used during the operation of localization array 811. Electromagnetic tracking system 810 may receive fiducial positions from localization array 811, and may further be connected to processing unit 107 so that the fiducial positions can be transmitted to processing unit 107. At processing unit 107, the fiducial positions can be used to control the movement of robotic arm 101.

Localization array 811 may also be affected by disturbances in the electromagnetic field, such that error is increased in the electromagnetically tracked positions of the implanted fiducials 106. X-ray imagers comprising X-ray sources 610 and X-ray detector panels 611 can be used to compensate for bias or offset caused by such electromagnetic disturbances. By using two X-ray imagers mounted approximately orthogonally, the 2D positions of the implanted fiducials 106 in the X-ray images can be back projected to obtain their 3D positions in the treatment room with high accuracy. The difference between the X-ray image-based fiducial positions and the fiducial positions determined using localization array 811 is thus the bias or offset of the electromagnetic tracking positions. This electromagnetic bias or offset may be calculated by processing unit 107, which receives the positions of implanted fiducials 106 as determined by the localization array 105 and the X-ray imaging system. The offset can then be used to correct the real-time electromagnetically tracked positions, as determined using the localization array 811. Any bias in the electromagnetically tracked positions can be corrected by taking occasional X-ray images to locate the implanted fiducials 106 with greater accuracy. The frequency of the X-ray images can be varied as necessary, for example, at every spatial position of the treatment delivery system (e.g., gantry or LINAC 102). New X-ray images could also be acquired whenever the electromagnetically tracked implanted fiducials 106 move beyond a certain positional threshold.

The resulting corrected positions of implanted fiducials 106 can be used by processing unit 107 to control robotic arm 101. Using these positions, processing unit 107 may direct robotic arm to aim LINAC 102 so that the beam of LINAC 102 intersects a treatment target that can be located by reference to the implanted fiducials 106.

Alternatively, treatment delivery system 100 may be a type of system other than a robotic arm-based system. For example, treatment delivery system 100 may be a gantry-based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry-based system may have a gimbaled radiation source head assembly.

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

Certain embodiments may be implemented as a computer program product that may include instructions stored on a computer-readable medium. These instructions may be used to program a general-purpose or special-purpose processor to perform the described operations. A computer-readable medium includes any mechanism for storing or transmitting information in a form (e.g., software, processing application) readable by a computer. The computer-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions.

Additionally, some embodiments may be practiced in distributed computing environments where the computer-readable medium is stored on and/or executed by more than one computer system. In addition, the information transferred between computer systems may either be pulled or pushed across the communication medium connecting the computer systems.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
    providing a localization array in a known position relative to a treatment couch, wherein the localization array is coupled to a positioning device of the treatment couch via an arm,
        wherein the positioning device is coupled to a platform attached to the treatment couch, and
        wherein the localization array and the positioning device are disposed below the treatment couch;
    maintaining the localization array at substantially the known position by controlling movement of the localization array by moving the arm coupled to the localization array; and
    moving the treatment couch independently of maintaining the position of the localization array wherein a detection field of the localization array continues to encompass at least one fiducial marker when moving the treatment couch.

2. The method of claim 1, wherein controlling the movement of the localization array comprises moving the treatment couch.

3. The method of claim 1, further comprising using the localization array to locate at least one fiducial marker.

4. The method of claim 1, wherein maintaining the localization array at substantially the known position comprises tolerating or compensating for deviations of the localization array from the known position.

5. The method of claim 1, further comprising:
    determining the known position for the localization array; and
    moving the localization array to substantially the known position.

6. The method of claim 5, wherein determining the known position comprises determining a position where a detection field of the localization array encompasses at least one fiducial marker.

7. The method of claim 5, wherein the known position is based on a characteristic of a signal received by the localization array from at least one fiducial marker.

8. The method of claim 5, wherein the known position for the localization array is chosen to avoid obstructing an imaging equipment or a moving equipment.

9. The method of claim 1, wherein maintaining the localization array at substantially the known position is performed for at least a portion of a treatment session.

* * * * *